United States Patent [19]

Manghisi et al.

[11] Patent Number: 4,948,797

[45] Date of Patent: Aug. 14, 1990

[54] 2,2-DISUBSTITUED 2,3-DIHYDRO-1,4-BENZODIOXIN DERIVATIVES HAVING HYPOTENSIVE ACTIVITY

[75] Inventors: Elso Manghisi; Aldo Salimbeni, both of Milan, Italy

[73] Assignee: Istituto Luso Farmaco D'Italia S.P.A., Milan, Italy

[21] Appl. No.: 269,773

[22] Filed: Nov. 9, 1988

[51] Int. Cl.$^5$ .................. A61K 31/505; C07D 405/14
[52] U.S. Cl. .................................. 514/254; 514/253; 544/291; 544/364; 544/371; 546/197; 546/199
[58] Field of Search ................ 544/291, 364, 377; 514/253, 254

[56] References Cited

U.S. PATENT DOCUMENTS

| | | | |
|---|---|---|---|
| 3,915,969 | 10/1975 | Manghisi et al. | 544/364 |
| 3,959,283 | 5/1976 | Lafon | 544/377 |
| 4,188,390 | 2/1980 | Campbell | 544/291 |
| 4,189,484 | 2/1980 | Mizogami et al. | 544/291 |
| 4,287,341 | 9/1981 | Hess et al. | 544/291 |
| 4,558,129 | 12/1985 | Kluge et al. | 544/377 |
| 4,788,290 | 11/1988 | Stack et al. | 544/377 |

*Primary Examiner*—Glennon H. Hollrah
*Assistant Examiner*—James H. Turnipseed
*Attorney, Agent, or Firm*—Bucknam and Archer

[57] ABSTRACT

2,2-Disubstituted 2,3-dihydro-1,4-benzodioxin derivatives of formula (I):

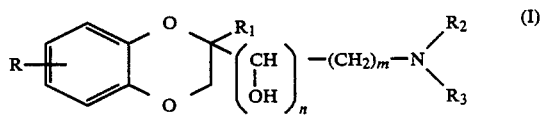

and pharmaceutically acceptable salts thereof having in vitro high affinity and selectively for $\alpha_1$ receptors and in vivo good and long lasting hypotensive activty, with negligible side-effects; processes for the preparation thereof and pharmaceutical compositions therefrom.

4 Claims, No Drawings

2,2-DISUBSTITUED 2,3-DIHYDRO-1,4-BENZODIOXIN DERIVATIVES HAVING HYPOTENSIVE ACTIVITY

The present invention relates to a series of compounds of general formula (I):

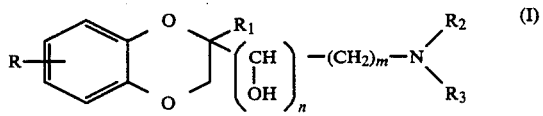

and to stereoisomers and optical isomers thereof, in which R is a hydrogen atom, one or more halogen atoms, one or more methyl, trifluoromethyl, hydroxy, methoxy, nitro, amino groups; $R_1$ is a $C_1$–$C_4$ straight or branched alkyl group, or a phenyl group (which can be unsubstituted or substituted at the phenyl ring by one or more halogen atoms or methyl, trifluoromethyl, hydroxy, methoxy, nitro or amino groups) or a $C_1$–$C_4$ straight or branched alkoxy group, optionally substituted by a hydroxy group; n can be 0 or 1; m can be an integer 1 to 3; when n=1, m is always=1;

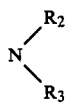

can be one of the following basic groups of formula:

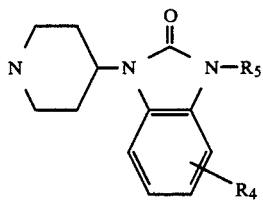

wherein $R_4$ can be hydrogen or one or more halogen atoms or one or more lower alkyl groups, while $R_5$ is hydrogen or a $C_1$–$C_4$ alkyl or alkoxyalkyl group or a $C_3$–$C_4$ alkenyl group;

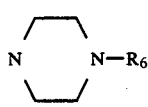

wherein $R_6$ is hydrogen, a phenyl group (unsubstituted or substituted at the aroxatic ring by one or more halogen atoms, or by methyl, trifluoromethyl, hydroxy, methoxy, nitro or amino groups), a 2-pyridyl group, a benzhydryl group (unsubstituted or substituted by one or more halogen atoms, methyl, methoxy) or a 4-amino-6,7-dimethoxyquinazolin-2-yl group or an acyl group such as acetyl, propionyl, benzoyl, 2-furoyl;

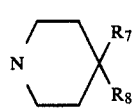

wherein $R_7$ can be hydrogen or hydroxy, while $R_8$ can be, depending on the meaning of $R_7$, hydrogen, a phenyl, benzoyl, benzamindo group, optionally substituted at the aromatic ring by one or more halogen atoms or methyl, trifluoromethyl, hydroxy, methoxy, nitro, amino groups.

The present invention also relates to the salts of compounds I with pharmaceutically acceptable inorganic acids such as hydrochloric, hydrobromic, nitric, sulfuric, phosphoric acid, as well as with pharmaceutically acceptable organic acids, such as acetic, propionic, maleic, fumaric, malic, tartaric, citric, methanesulphonic and the like.

The present invention further relates to the processes for the preparation of the compounds of general formula I.

The compounds of the present invention provide a remarkable advantage in comparison with the prior art, from both the chemical and pharmacological point of view. In fact, disubstitution at the 2-position of 1,4-benzodioxane ring gives the compounds a higher stability of the heterocyclic ring against some chemical agents (unlike the monosubstituted compounds which can undergo ring cleavage, as described, for instance, by V. Rosnati, A. Salimbeni, Tetrahedron, 16, 4541, 1986) and surprisingly changes the pharmacological action spectrum, increasing affinity and selectivity for $\alpha_1$ receptors and particularly removing some side-effects (related to hearth rate and CNS), thus allowing to have more convenient products for therapeutical use.

In the following disclosure, R, $R_1$, $R_2$, $R_3$, n, m have the above mentioned meanings.

In a first method for the preparation of compounds of formula I, a compound of formula (II):

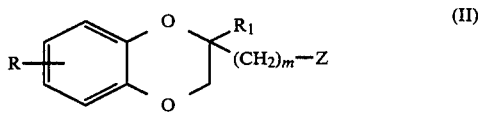

wherein Z is a hydroxy group, esterified with a strong inorganic or organic acid (such as hydrochloric, hydrobromic, hydroiodic, sulfuric, p-toluenesulfonic and the like), is reacted with an amine of formula (III):

The reaction is generally carried out in an apolar organic solvent, such as benzene, toluene, xilene, in the presence of an amine excess, at the boiling temperature of the solvent. When Z is a hydroxy group esterified with an aromatic sulfonic acid, it is advisable to effect the reaction in aprotic high-boiling solvents, such as dimethylsulfoxide, N,N-dimethylformamide and the like, in the presence of an alkali carbonate, such as $Na_2CO_3$ or $K_2CO_3$, at a temperature of 100°–120° C.

In a second method for the preparation of compounds of formula I, corresponding compounds of formula (IV):

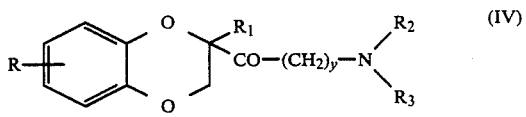

wherein y can be an integer 1 to 2, are subjected to reduction.

In particular, when in formula I a hydroxyalkyl group is present (n=1), reduction is carried out, for example, with hydrogen and palladium or with NaBH4 in methanol solution, while when in formula I no hydroxyalkyl groups are present (n=0), reduction can be effected with catalytically activated hydrogen or by treatment with p-toluenesulfonylhydrazine and sodium cyanoborohydride.

In a third method for the preparation of compounds of formula I, in which a hydroxyalkyl group (n=1) is present, compounds of formula (V):

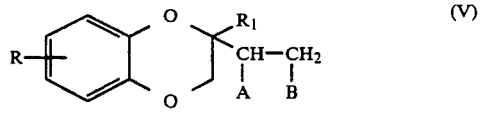

wherein A and B are together an oxygen atom or A is a hydroxy group and B is a chlorine or bromine atom, are reacted With amines of formula 111, in an organic solvent (such as acetone, methylethylketone, dioxane, ethanol) at the boiling temperature of the solvent, or in an aprotic high-boiling solvent, such as dimethylformamide, in the presence of an alkali carbonate, at a temperature of 100°-120° C.

Intermediates II, IV and V are not known in literature, but they can be obtained by per se known methods, as described in the Examples. Intermediates II, for instance, can easily be prepared by reduction with lithium alluminium hydride of the corresponding methyl- or ethyl-esters of 1,4-benzodioxan-2-yl-acetic acids to alcohols and subsequent esterification with strong inorganic or organic acids, HZ, (such as hydrochloric, hydrobromic, hydroiodic, sulfuric, p-toluenesulfonic and the like) under anhydrous conditions, or with halides or anhydrides of said acids, such as thionyl chloride or p-toluene-sulfonyl chloride. Intermediates of formula IV can be obtained, for example, by reaction of haloketones of formula (VI):

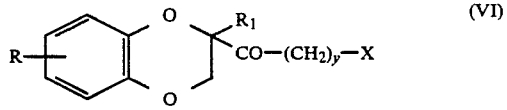

wherein X=Cl, Br, I and y can be an integer 1 to 2, with corresponding amines of formula III, in methanol, in the presence of a proton acceptor such as triethylamine or carrying out the reaction in an apolar organic solvent (such as benzene, toluene and the like) in the presence of an amine excess, at the solvent's boiling temperature. Intermediates of formula V, wherein A is a hydroxy group and B is a chlorine or bromine atom, can be obtained by reduction of haloketones VI (in which y=1) for example with NaBH4 in methanol solution. Finally, intermediates of formula V, in which A and B are together an oxygen atom, can be obtained either by epoxydation with organic peracids (such as perbenzoic acid, m-chloroperbenzoic acid and the like) in chloroform solution, at room temperature, of corresponding alkenyl derivatives of formula (VII):

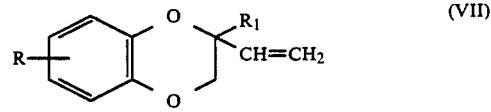

or by cyclization with alkali of the above halohydrines of formula V, in which A is a hydroxy group and B is a chlorine or bromine atom.

When geometric or optic isomeric mixtures of compounds of formulae I, II, IV-VII, are obtained, these can be separated into the single isomers by means of per se known methods (e.g. fractional distillation, crystallization and/or chromatography).

The compound object of the present invention show in vitro a high affinity for the $\alpha_1$ receptors and a not so prominent action on the $\alpha_2$ receptors, determined in respect of [$^3$H]-Prazosin and [$^3$H]-Clonidine respectively, using the method reported by P Greengrass, R. Bremner, Eur. J. Pharmacol 55, 323 (1979) and D. C. U. Prichard et al, Mol. Pharmacol 13, 454 (1977), while in vivo they seem to have a low toxicity and a good and durable anti-hypertensive activity, determined in the SHR rat by oral route, with the method reported by J Pfeffer et al, J. Lab. Clin. Med. 78, 957 (1971).

The biological properties of some of the compounds are reported herewith as example. Compound [1(2-(2,3-di- hydro-2-methyl-1,4-benzodioxin-2-yl)-2-hydroxyethyl)-4-piperidinyl]-1,3-dihydro-2H-benzimidazole-2-one (described in example 3) possesses a $IC_{50}$ for the $\alpha_1$ receptors of $5.5 \times 10^{-8}M$ and a $IC_{50}$ for the $\alpha_2$ receptors of $1.8 \times 10^{-5}M$, has a toxicity, expressed as $LD_{50}$, of about 1000 mg/kg/os and causes a reduction of the pressure of 21% at a 20 mg/kg/os dosage without significantly varying the heart rate. Compound 1-(4-amino-6,7-dimethoxyquinazoline-2-yl)-4-[2-(2,3-dihydro-2-methyl-1,4-benzodioxin-2-yl)-2-hydroxyethyl]-piperazine hydrochloride (described in example 6) possesses a $IC_{50}$ for the $\alpha_1$ receptors of $3.6 \times 10^{-9}M$ and a $IC_{50}$ for the $\alpha_2$ receptors $>10^{-5}M$, has a toxicity, expressed as $LD_{50}, >2000$ mg/kg/os and causes a reduction in the pressure of 20%, at a 30 mg/kg/os dosage without significantly modifying the heart rate.

The compounds object of the present invention can therefore be usefully used in human therapy for the treatment of cardiovascular diseases, in particular hypertension.

The compounds can be administered by parenteral and oral routes by means of suitable pharmaceutical formulations such as vials, syrups, drops, jelly pills, tablets and so on.

Daily dosage of administration varies according to the administration route chosen as well as to the gravity of the disease Anyhow, an effective dosage is comprised between 0.1-10 mg/kg/day, preferably 0.5-5 mg/kg/day.

The following examples illustrate the invention without limiting it in any way. Boiling and melting points are not corrected. The identity of the substances and their purity have been established through elementar analysis (C, H, N) and through IR, UV and NMR spectroscopy.

Stereoisomer racemic forms present in the compounds having two asymmetric carbon atoms (e.g. in compounds I in which $R_1=CH_3$ and n=1), have been marked with A and B letters. In NMR spectrum they differ for the different "chemical shift" ($\delta$) of the methyl group at the 2-position of 1,4-benzodioxane ring. In the following Examples, the compounds having a δCH$_3$ at high fields ($\approx$1.2 ppm) are defined "racemate A", while those having a δCH$_3$ at low fields ($\approx$1.3 ppm) are defined "racemate B".

EXAMPLE 1

1-[1-[2-(2,3-dihydro-2-methyl-1,4-benzodioxin-2-yl)-ethyl[-4-piperidinyl]-1,3-dihydro-2H-benzimidazol-2-one (a) 180 g of ethyl (2,3-dihydro-2-methyl-1,4-benzodioxin-2-yl)acetate [J. Org. Chem. 39, 1808 (1974)] dissolved in 300 ml of anhydrous ether was added dropwise to a solution of 24.2 g of LiAlH$_4$ in 3 l of anhydrous ether. When the addition was completed, the mixture was refluxed for 12 hours, then humid ether and water were carefully added thereto. The mixture was filtered and dried and the residue was distilled. The fraction boiling at 126°-130°/1 mm Hg corresponds to (2,3-dihydro-2-methyl-1,4-benzodioxin-2-yl)ethanol.

(b) A solution of 36 g of the above alcohol in 40 ml of anhydrous pyridine was cold treated with 15 ml of SOCl$_2$ and refluxed for 2 hours, then cooled and poured into ice-water. The mixture was extracted with ethyl ether, washed with a NaHCO$_3$ saturated solution and with water, then dried. Solvent was distilled off under vacuum. The residual oil was distilled: the fraction having b.p. 135°-140°/0.2 mm Hg was 2-(2-chloroethyl)-2,3-dihydro-2-methyl-1,4-benzodioxin.

(c) A mixture of 6.5 g of 2-(2-chloroethyl)-2,3-dihydro-2-methyl-1,4-benzodioxin, 5.3 g of 4-(2-keto-1benzimidazolinyl)piperidine, 6.4 g of K$_2$CO$_3$, 0.1 g of KI in 60 ml of toluene was refluxed for 50 hours. The solid was filtered and the solution was evaporated to dryness. The residual oil was dissolved in ethyl ether and the obtained solution was treated with a HBr alcoholic solution. The obtained solid was crystallized from methanol/ethyl ether; m.p. 226°-228° C.

Anagously, the following compound was prepared: 1-[2-(2,3-dihydro-2-methyl-1,4-benzodioxin-2-yl)ethyl]-4-(2-methoxyphenyl)piperazine hydrochloride (p.f. 172°-174° C., from ethanol).

EXAMPLE 2

5-chloro-1-[1-[2-(2 3-dihydro-2-methyl-1,4-benzodioxin-2-yl)-ethyl]-4-piperidinyl]-1,3-dihydro-2H-benzimidazol-2-one (a) A solution of 54 g of p-toluenesulfonylchloride in 30 ml of anhydrous pyridine was cald added to 50 g of (2,3-dihydro-2-methyl-1,4-benzodioxin-2-yl)-ethanol (prepared as described in Example 1) dissolved in 130 ml of anhydrous pyridine. After 24 hours at 0°-5° C., the mixture was poured into ice-water The obtained solid, i.e. 2,3-dihydro-2-methyl-2-tosyloxy-ethyl-1,4-benzodioxin, was filtered and crystallized from ethanol; m.p. 68°-70° C.

(b) A mixture of 8.2 g of 2,3-dihydro-2-methyl-2-tosyloxy-ethyl-1,4-benzodioxin, 5 g of 4-(2-keto-5-chloro-1-benzimidazolinyl)piperazine, 12 g of Na$_2$CO$_3$ in 130 ml of 4-methyl-2-pentanone was refluxed for 10 hours, then filtered and evaporated to dryness. The residual oil was dissolved in ethyl ether and the obtained solution was treated with a HCl ethanol solution. The resulting solid was crystallized from chloroform-ethyl ether, m.p. 118°-120° C.

Analogously, the following compounds were obtained:

4-benzamido-1-[2-(2,3-dihydro-2-methyl-1,4-benzodioxin-2-yl)ethyl]piperidine hydrochloride, m.p. 270° C. (from 85% ethanol);

4-(4-fluorobenzoyl)-1-[2-(2,3-dihydro-2-methyl-1,4-benzodioxin-2-yl)ethyl]piperidine hydrochloride, m.p. 205°-207° C. from ethanol).

EXAMPLE 3

1-[2-(2,3-dihydro-2-methyl-1,4-benzodioxin-2-yl)-2-hydroxy-ethyl]-4-piperidinyl]-1,3-dihydro-2H-benzimidazol-2-one (a) (2,3-dihydro-2-methyl-1,4-benzodioxin-2-yl)carboxylic acid was prepared as described in J. Heterocyclic Chem. 17, 489 (1980): m.p. 126°-128° C. (from benzene).

Analogously, the following compounds were obtained:

(6-chloro-2,3-dihydro-2-methyl-1,4-benzodioxin-2-yl)-carboxylic acid, m.p. 182°-185° C. (from benzene);

(7-chloro-2,3-dihydro-2-methyl-1,4-benzodioxin-2-yl)carboxylic acid, m.p. 160°-163° C. (from benzene);

(6,7-dichloro-2,3-dihydro-2-methyl-1,4-benzodioxin-2-yl)-carboxylic acid, m.p. 174°-176° C. (from benzene);

(2,3-dihydro-2-methyl-6-methoxy-1,4-benzodioxin-2-yl)carboxylic acid, m.p. 136°-138° C. (from benzene);

(2,3-dihydro-2-methyl-6,7-dimethoxy-1,4-benzodioxin-2-yl)-carboxylic acid, m.p. 146°-148° C. (from toluene);

(2-ethyl-2,3-dihydro-1,4-benzodioxin-2-yl)-carboxylic acid, m.p. 120°-121° C. (from benzene-hexane);

(2-methyl-7-nitro-2,3-dihydro-1,4-benzodioxin-2-yl)carboxylic acid, m.p. 185°-187° C. (from ethyl ether).

(b) 38 ml of SOCl2 was added to a solution of 24,3 g of (2,3-dihydro-2-methyl-1,4-benzodioxin-2-yl)-carboxylic acid in 700 ml of anhydrous benzene. The mixture was refluxed for 2 hours, then solvent was removed off under vacuum. The solid residue, i.e. (2,3-dihydro-2-methyl-1,4-benzodioxin-2-yl)-carboxilic acid chloride, was used directly for the subsequent reaction.

Analogously, (6-chloro-2,3-dihydro-2-methyl-1,4-benzodioxin-2-yl)-carboxylic acid chloride was prepared.

(c) 13.9 g of the above acyl chloride, dissolved in 100 ml of anhydrous ether, was added to 2.5 l of a 0.055 N diazomethane ether solution, cooled to 2° C. After 18 hours a gaseous HCl stream was bubbled for 4 hours into the solution, cooled to 0° C. The mixture was poured into ice and the ether phase was separated, washed with a NaHCO$_3$ saturated solution and water, then dried and evaporated to dryness. The residue of 2-chloroacetyl-2,3-dihydro-2-methyl-1,4-benzodioxin was crystallized from hexane, m.p. 76°-79° C.

Analogously, the following compound was prepared: 6-chloro-2-chloroacetyl-2,3-dihydro-2-methyl-1,4-benzodioxin, m.p. 79°-80° C. (from hexane).

(d) 1.25 g of NaBH$_4$ was added portionwise to a solution of 14 g of 2-chloroacetyl-2,3-dihydro-2-methyl-1,4-benzodioxin, cooled to −5° C. After the addition, the mixture was stirred for 1 hour, then neutralized with glacial acetic acid and solvent was removed under vacuum. The residue was taken up into water and ethyl ether. The ether phase was separated, dried and evaporated to dryness. The residual oil, i.e. the mixtures of racemates A and B of α-(chloromethyl)-2,3-dihydro-2-methyl-1,4-benzodioxin-2-methanol, was directly used for the next reaction.

Analogously, the following compound was prepared:

6-chloro-α-(chloromethyl)-2,3-dihydro-2-methyl-1,4-benzodioxin-2-methanol (mixture of racemates A and B).

By crystallization from hexane, racemate A was obtained (m.p. 106°-108° C.).

(e) A mixture of 4.5 g of α-(chloromethyl)-2,3-dihydro-2-methyl-1,4-benzodioxin-2-methanol, 3.4 g of 4-(2-keto-1-benzimidazolinyl)piperidina, 4,1 g of K$_2$CO$_3$, 0.1 g of KI in 100 ml of toluene was refluxed for 28 hours. The solid was filtered and evaporated to dryness. The residual oil was dissolved in ethyl ether and the obtained solution was treated with a HCl alcohol solution. The resulting solid was crystallized from methanol/ethyl ether, m.p. 140°-143° C. (mixture of racemates A and B).

Analogously, the following compounds were prepared:

5-chloro-1-[1-[2-(2,3-dihydro-2-methyl-1,4-benzodioxin-2-yl)-2-hydroxyethyl]-4-piperidinyl]-1,3-dihydro-2H-benzimidazol-2-one hydrochloride (mixture of racemates A and B); m.p. 175°-177° C. (from chloroform/ether).

1-[1-[2-(6-chloro-2,3-dihydro-2-methyl-1,4-benzodioxin-2-yl)-2-hydroxyethyl]-4-piperidinyl]-1,3-dihydro-2H-benzimidazol-2-one tartrate (racemate A); m.p. 156°-158° C. (from chloroform/ether).

1-[1-[2-(2-ethyl-2,3-dihydro-1,4-benzodioxin-2-yl)-2-hydroxyethyl]-4-piperidinyl]-1,3-dihydro-2H-benzimidazol-2-one hydrochloride hemihydrate (m.p. 185°-190° C., from ethanol/ether).

EXAMPLE 4

1-[1-[2-(7-chloro-2,3-dihydro-2-methyl-1,4-benzodioxin-2-yl)-2-hydroxyethy]-4-piperidinyl]-1,3-dihydro-2H-benzimidazol-2 one (a) 80 ml of a 2M MeLi-LiBr solution in ethyl ether was added dropwise, under nitrogen stream, to a solution of 17.7 g of (7-chloro-2,3-dihydro-2-methyl-1,4-benzodioxin-2-yl)carboxylic acid (prepared as described in Example 3) dissolved in 420 ml of anhydrous ethyl ether. The reaction mixture was refluxed for 1 hour, then poured into 200 ml of a NH$_4$Cl saturated solution. The separated ether phase was washed with NaHCO$_3$ and water, then dried. Solvent was removed under vacuum. After distillation, 2-acetyl-7-chloro-2,3-dihydro-2-methyl-1,4-benzodioxin (b.p. 168°-173° C. 0.6 mm Hg) was obtained.

Analogously, the following compounds were obtained:

2-acetyl-2,3-dihydro-2-methyl-1,4-benzodioxin (b.p. 120°-125° C./0.8 mm Hg);

2-acetyl-6-chloro-2,3-dihydro-2-methyl-1,4-benzodioxin (m.p. 50°-52° C., from hexane);

2-acetyl-6,7-dichloro-2,3-dihydro-2-methyl-1,4-benzodioxin (m.p. 52°-54° C., from hexane);

2-acetyl-2,3-dihydro-2-methyl-6-methoxy-1,4-benzodioxin (oil);

2-acetyl-2,3-dihydro-2-methyl-6,7-dimethoxy-1,4-benzodioxin (m.p. 87-88° C, from isopropanol).

(b) 9.7 g of bromine was added to a solution of 13.8 g of 2-acetyl-7-chloro-2,3-dihydro-2-methyl-1,4-benzodioxin in 350 ml of anhydrous ether at 10° C. After the addition, the mixture was stirred for 2 hours, then washed with a NaHCO$_3$ saturated solution and water. After drying, solvent was removed off under vacuum. The residual oil, i.e. 2-bromoacetyl-7-chloro-2,3-dihydro-2-methyl-1,4-benzodioxin, was distilled, b.p. 195°-200° C./2.2 mm Hg.

Analogously, the following compounds were obtained:

2-bromoacetyl-2,3-dihydro-2-methyl-1,4-benzodioxin (m.p. 58°-59° C., from hexane);

2-bromoacetyl-6-chloro-2,3-dihydro-2-methyl-1,4-benzodioxin (m.p. 90°-92° C., from hexane);

2-bromoacetyl-6,7-dichloro-2,3-dihydro-2-methyl-1,4benzodioxin (m.p. 73°-76° C., from hexane);

2-bromoacetyl-2,3-dihydro-2-methyl-6-methoxy-1,4-benzodioxin (oil);

2-bromoacetyl-2,3-dihydro-2-methyl-6,7-dimethoxy-1,4benzodioxin.

(c) 1.3 g of NaBH$_4$ was cald added portionwise to a solution of 15 g 2-bromoacetyl-7-chloro-1,3-dihydro-2-methyl-1,4-benzodioxin in 400 ml of absolute ethanol. The mixture was stirred for 2 hours, then worked up as described in Example 3. 2-Bromo-1(7-chloro-2,3-dihydro-2-methyl-1,4-benzodioxin-2yl)ethanol was obtained, in form of a mixture of racemates A and B, which was directly used.

Analogously, the following compounds were prepared:

2-bromo-1-(2,3-dihydro-2-methyl-1,4-benzodioxin-2-yl)-ethanol. By column chromatography (silica gel), eluting with benzene/hexane 8:2, racemate A (m.p. 80°-82° C.) and racemate B (m.p. 74°-76° C.) were prepared.

2bromo-1-(6-chloro-2,3-dihydro-2-methyl-1,4-benzodioxin-2-yl)ethanol. By crystallization from benzene, racemate A (m.p. 133°-135° C.) was isolated.

2-bromo-1-(6,7-dichloro-2,3-dihydro-2-methyl-1,4-benzodioxin-2-yl)ethanol. By crystallization from benzenehexane, racemate A (m.p. 92°-94° C.) was obtained.

2-bromo-1-(2,3-dihydro-2-methyl-6-methoxy-1,4-benzodioxin-2-yl)ethanol (oil).

2-bromo-1-(2,3-dihydro-2-methyl-6,7-dimethoxy-1,4-benzodioxin-2-yl)ethanol (m.p. 109°-110° C., from benzene-hexane).

(d) A mixture of 6 g of 2-bromo-1-(7-chloro-2,3-dihydro-2-methyl-1,4-benzodioxin-2-yl)ethanol, 3.4 g of 4-(2-keto-1-benzimidazolinyl)piperidine, 6.3 g of Na$_2$CO$_3$ in 100 ml of anhydrous dimethylformamide was refluxed for 11 hours, then poured into 1.5 l of water, extracted with chloroform, washed with water and dried. Solvent was evaporated off under vacuum, the residue was dissolved in isopropanol and treated with an equimolecular amount of maleic acid dissolved in isopropanol. The obtained solid was crystallized form isopropanol; racemate A was obtained in form of maleate hemiisopropanolate emihydrate; m.p. 198°-200° C.

Analogously, the following compounds were obtained:

1-[1-[2-(2,3-dihydro-2-methyl-1,4-benzodioxin-2-yl)-2hydroxyethyl]-4-piperidinyl]-1,3-dihydro-2H-benzimidazol-2-one hydrochloride (racemate A); (m.p. 277°-279° C., from methylethylketone);

1-[1-[2-(2,3-dihydro-2-methyl-1,4-benzodioxin-2-yl)-2hydroxyethyl]-1,3-dihydro-2H-benzimidazol-2-one]-maleate (with 0.33 mole of crystallization isopropanol); (racemate B) (m.p. 120°-122° C.; from isopropanol);

5-chloro-1-[1-[2-(2,3-dihydro-2-methyl-1,4-benzodioxin-2-yl)-2-hydroxyethyl]-4-piperidinyl]-1,3-dihydro-2H-benzimidazol-2-one hydrochloride hemihydrate (racemate A); (m.p. 191°-193° C., from methylethylketone);

5-chloro-1-[1-[2-(7-chloro-2,3-dihydro-2-methyl-1,4-benzodioxin-2-yl)-2-hydroxyethyl]-4-piperidinyl]-1,3-dihydro-2H-benzimidazol-2-one hydrochloride (mixture of racemates A and B); (m.p. 160°-165° C., from methanol-ethyl ether);

11-[1-[2-(6,7-dichloro-2,3-dihydro-2-methyl-1,4-benzodioxin-2-yl)-2-hydroxyethyl]-4-piperidinyl]-1,3-dihydro-2H-benzimidazol-2-one hydrochloride (contains 0.25 mole of crystallization ether) (mixture of racemates A and B); (m.p. 165°-170° C., from methanol-ethyl ether);

1-[1-[2-(2,3-dihydro-2-methyl-6-methoxy-1,4-benzodioxin-2-yl)-2-hydroxyethyl]-4-piperidinyl]-1,3-dihydro-2H-benzimidazol-2-one citrate hydrate (m.p. 170°-175° C., from abs. EtOH);

-1-[1-[2-(2,3-dihydro-2-methyl-6,7-dimethoxy-1,4-benzodioxin-2-yl)-2-hydroxyethyl]-4-piperidinyl]-1,3-dihydro-2H-benzimidazol-2-one maleate (m.p. 130°-135° C., from isopropanol-ether);

1-[2-hydroxy-2-(2,3-dihydro-2-methyl-1,4-benzodioxin-2yl)ethyl]-4-(2-methoxyphenyl)piperazine hydrochloride (m.p. 252°-254° C., from abs. ethanol);

4-benzamido-1-[2-hydroxy-2-(2,3-dihydro-2-methyl-1,4-benzodioxin-2-yl)ethyl]-piperidine hydrochloride (m.p. 270° C, from 85% ethanol);

1-[2-methyl-1,4-benzodioxin-2-yl)-2-hydroxyethyl]-4-(2-piridyl)piperazine maleate (m.p. 170°-173° C., from ethanol);

4-[4-fluorobenzoyl-[1-[2-(2,3-dihydro-2-methyl-1,4-benzodioxin-2-yl)-2-hydroxyethyl]piperidine hydrochloride (m.p. 260°-262° C., from methanol);

4-furoyl-1-[1-(2,3-dihydro-2-methyl-1,4-benzodioxin-2-yl)-2-hydroxyethyl]piperazine maleate (m.p. 172°-174° C., from ethanol);

4-benzhydryl-1-[1-(2,3-dihydro-2-methyl-1,4-benzodioxin-2-yl)-2-hydroxyethyl]-piperazine dihydrochloride (m.p. 220°-222° C., from ethanol-ether).

EXAMPLE 5

1-[2-(2,3-dihydro-2-methyl-1,4-benzodioxin-2-yl)-2-hydroxyethyl]-4-piperidinyl]-1,3-dihydro-2H-benzimidazol-2-one (a) A solution of 6 g of 2-bromoacetyl-2,3-dihydro-2-methyl-1,4-benzodioxin (prepared as described in Example 4, step b), 4.5 g of 4-(2-keto-1-benzimidazolinyl)-piperidine, 2.1 g of triethylamine in 60 ml of absolute ethanol was refluxed for 14 hours. Solvent was removed under vacuum, the residue was treated with water, then extracted with chloroform. The chloroform phase was dried, then evaporated to dryness. The residue, 1-[1-[(2,3-dihydro-2-methyl-1,4-benzodioxin-2-yl)-2-oxoethyl]-4-piperidinyl]-1,3-dihydro-2H-benzimidazol-2-one was treated with hexane and directly used for the subsequent step.

(b) 0.1 g of NaBH₄ was added portionwise to a solution of 1.5 g of 1-[1-[(2,3-dihydro-2-methyl-4-benzodioxin-2-yl)-2-oxoethyl]-4-piperidinyl]-1,3-dihydro-2-benzimidazol-2-one in 30 ml of absolute methanol, cooled to −5° C. After the addition, the mixture was stirred for 5 hours, then cald neutralized with glacial acetic acid and evaporated to dryness. The residue was treated with water and extracted with methylene chloride. After drying, solvent was distilled off under vacuum. From the residue, the hydrochloride was prepared as described in example 3.

EXAMPLE 6

1-[2-(2,3-dihydro-2-methyl-1,4-benzodioxin-2-yl)-2-hydroxyethyl]-4-piperidinyl]-1,3-dihydro-2H-benzimidazol-2-one (a) A mixture of 59 g of 2,3-dihydro-2-methyl-2-tosyloxyethyl-1,4-benzodioxin, 300 ml of 48% aqueous HBr, 1200 ml of ethanol was refluxed for 16 hours, then concentrated to small volume, neutralized with Na₂CO₃ and extracted with ethyl ether. The ether solution, after repeated washings with water and drying, was evaporated to dryness. The residual oil, i.e. 2-(2-bromoethyl)-2,3-dihydro-2-methyl-1,4-benzodioxin, was distilled, b.p. 160°-170° C./1 mm Hg.

(b) A mixture of 40 g of the above bromo-derivative, 15.5 g of KOH in drops, 350 ml of ethanol was refluxed for 2 hours, then evaporated to dryness. The residue was taken up in water and ethyl ether and the ether phase was separated, dried and evaporated to dryness. The residual oil, i.e. 2-ethenyl-2,3-dihydro-2-methyl-1,4-benzodioxin, was distilled; b.p. 105°-110° C./3 mm Hg.

(c) A solution of 2.25 g of m-chloroperbenzoic acid in 40 ml of methylene chloride was added dropwise to a solution of 1.7 g of the above unsaturated compound in 20 ml of methylene chloride. After 24 hours the mixture was filtered, washed with a sodium metabisulfite solution (2.5 g in 25 ml of water). The organic phase was dried and evaporated to dryness. The residual oil, i.e. 2,3-dihydro-2-methyl-2-oxyranyl-1,4-benzodioxin (as a mixture of the racemates A and B), was directly used for the subsequent step.

(d) A mixture of 1.9 g of 2,3-dihydro-2-methyl-2-oxyranyl-1,4-benzodioxin, 1.8 g of 4-(2-keto-1-benzimidazolinyl)piperidine in 20 ml of absolute ethanol was refluxed for 12 hours. Solvent was removed off under vacuum. The hydrochloride of the residue was prepared as described in Example 3.

Analogously, the following compounds were prepared:

1-carbethoxy-4-[2-(2,3-dihydro-2-methyl-1,4-benzodioxin-2-yl)-2-hydroxyethyl]-piperazine hydrochloride (m.p. 175°-177° C., from ethylacetate);

1-[2-(2,3-dihydro-2-methyl-1,4-benzodioxin-2-yl)-2-hydroxyethyl]-piperazine hydrochloride (m.p. 259°-261° C., from ethanol-ether); 1-(4-amino-6,7-dimethoxyquinazolin-2-yl)-4-[2-(2,3-dihydro-2-methyl-1,4-benzodioxin-2-yl)-2-hydroxyethyl]-piperazine hydrochloride (m.p. 210°-215° C., from isoamylalcohol).

EXAMPLE 7

1-[1-(2-(2,3-dihydro-2-methoxy-1,4-benzodioxin-2-yl)-2-hydroxyethyl)-4-piperidinyl]-1,3-dihydro-2H-benzimidazol-2-one maleato (a) A solution of 3.8 g of 2-acetyl-2-bromo-2,3-dihydro-1,4-benzodioxin (prepared according to Gazz. Chim. Ital. 103, 79 (1973)) in 38 ml of methanol was refluxed for 30 minutes. Solvent was removed under vacuum, and the residue was dissolved in methylene chloride and washed with a diluted NaHCO₃ solution and water till neutral. Solvent was removed under vacuum and the residual oil was distilled under vacuum (b.p. 130°-140° C./0.8 mm Hg).

Analogously, the following compound was prepared:
2-acetyl-2-ethoxy-2,3-dihydro-1,4-benzodioxin (p.f. 44°-45° C., from hexane.

(b) To a solution of 1.5 g of 2-acetyl-2,3-dihydro-2-methoxy-1,4-benzodioxin in 40 ml of anhydrous ether, 1.1. g of bromine was added dropwise, at 0°-5° C. After the addition, the reaction mixture was stirred for 2 hours, then washed with a NaHCO3 and water. After drying, solvent was evaporated off under vacuum. The residual oil, i.e. 2-bromoacetyl-2,3-dihydro-2-methoxy-1,4-benzodioxin, was directly used for the next reaction.

(c) 12 g of NaBH4 was added at −5° C. to a solution of 1.7 g of the bromoketone described in step (b), in 60 ml of anhydrous methanol. The mixture was stirred for 1.5 hours. After the usual working up, as described in step, (c) of Example 4, 1.6 g of 2-(2-bromoethyl-1-hydroxy)-2,3-dihydro-2-methoxy-1,4-benzodioxin, was obtained in form of an oil which was directly used for the subsequent step.

(d) A mixture of 1.18 g of the above bromohydrine, 0.7 g of 4-(2-keto-1-benzimidazolinyl)piperidine, 1.1 g of Na2CO3 in 21 ml of anhydrous DMF was refluxed for 8 hours, then poured into water and extracted with chloroform. The organic phase was washed with water, dried and evaporated to dryness. The residue was dissolved in isopropanol and treated with an equimolecular amount of maleic acid. The obtained solid was crystallized from methanol-ether, m.p. 143°-144° C.

Analogously, the following compound was prepared:
1-[1-(2-(2-ethoxy-2,3-dihydro-1,4-benzodioxin-2-yl)-2-hydroxyethyl)-4-piperidinyl]-1,3-dihydro-2H-benzimidazol-2-one hydrochloride (m.p. 177°-179° C., from acetone-ethyl ether).

EXAMPLE 8

1-(4-amino-6,7-dimethoxyquinazolin-2-yl)-4-[(2,3-dihydro2-methyl-1,4-benzodioxin-2-yl)methyl]-piperazine The compound, in form of the hydrochloride, was prepared according to Example 2, starting from 2,3-dihydro-2-methyl-2-tosyloxymethyl-1,4-benzodioxin (prepared according to J. Heterocyclic Chem. 17, 489 (1980) and 1-(4-amino-6,7-dimethoxyquinazolin-2-yl)piperazine; m.p. 255° C. (from methanol).

We claim:

1. A compound of formula (I):

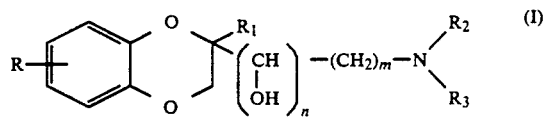

and to stereoisomers and optical isomers thereof, wherein R is hydrogen, at least one halogen atom, at least one methyl, trifluoromethyl, hydroxy, methoxy, nitro or amino group; $R_1$ is a $C_1$-$C_4$ straight or branched alkyl or phenyl unsubstituted or phenyl substituted by (a) at least one halogen atom, (b) methyl, (c) trifluoromethyl, (d) hydroxy, (e) methoxy, (f) nitro or (g) amino groups or $R_1$ is a $C_1$-$C_4$ straight or branched alkoxy which is unsubstituted or substituted by hydroxy group; n is O or 1; m is an integer 1 to 3; when n=1, m is always=1;

is a basic group of formula:

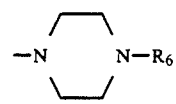

wherein $R_6$ is hydrogen, phenyl unsubstituted or substituted by (a) at least one halogen or by (b) methyl, (c) trifluoromethyl, (d) hydroxy, (e) methoxy, (f) nitro or (g) amino group, or $R_6$ is a 2-pyridyl, a benzyhydryl group unsubstituted or substituted by (a) at least one halogen, (b) methyl, (c) methoxy or $R_6$ is 4 amino-6,7-dimethoxyquinazolin-2-yl group or acetyl, propionyl, benzoyl or 2-furoyl and a salt thereof with a pharmaceutically acceptable inorganic or organic acid.

2. 1-(4-amino-6,7-dimethoxyquinazolin-2-yl)-4-[2-(2,3-dihydro-2-methyl-1,4-benzodioxin-2-yl)-2-hydroxyethyl]-piperazine hydrochloride in the racemic and optically active forms thereof, and pharmaceutically acceptable salts thereof.

3. 1-(4-amino-6,7-dimethoxyquinazolin-2-yl)-4-[(2,3-dihydro-2 -methyl-1,4-benzodioxin-2-yl)methyl]-piperazine in the racemic and optically active forms thereof, and pharmaceutically acceptable salts thereof.

4. Pharmaceutical compositions having antihypertensive activity, containing as the active ingredient a compound according to claim 1, in form of free bases or pharmaceutically acceptable salts.

* * * * *